| United States Patent [19] | [11] 4,002,646 |
| --- | --- |
| Robinson | [45] Jan. 11, 1977 |

[54] PROCESS FOR MAKING TETRAHYDROFURANS

[75] Inventor: Ivan Maxwell Robinson, Wilmington, Del.

[73] Assignee: E. I. Du Pont de Nemours and Company, Wilmington, Del.

[22] Filed: July 17, 1975

[21] Appl. No.: 596,647

[52] U.S. Cl. ............... 260/346.1 R; 204/158 HA; 260/632 R
[51] Int. Cl.² ................................. C07D 307/08
[58] Field of Search ............... 260/346.1, 632 R; 204/158 HA

[56] References Cited

OTHER PUBLICATIONS

Deno et al., J. Org. Chem., vol. 39, pp. 520–23, (1974).

*Primary Examiner*—John D. Randolph

[57] ABSTRACT

Tetrahydrofurans are produced by (a) contacting gamma-chloroalkanols with an aqueous protonic solution by which the chloroalkanol is cyclized to form a tetrahydrofuran and (b) removing the resultant tetrahydrofuran from the reaction mixture. The gamma-chloroalkanol is preferably derived by free radical chlorination of alkanols in the presence of 50–96% wt. sulfuric acid.

9 Claims, 1 Drawing Figure

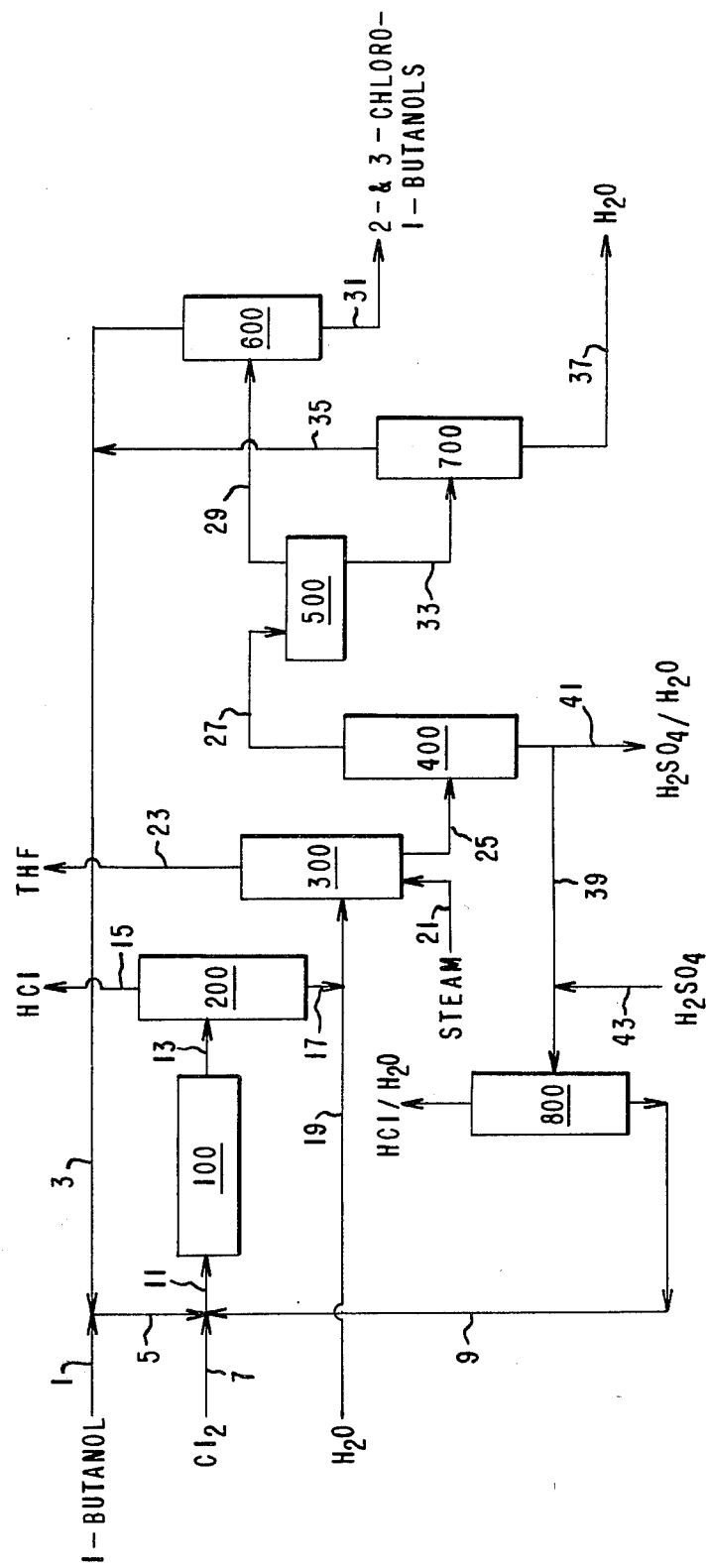

PROCESS FOR MAKING TETRAHYDROFURANS

Commercially, THF is usually made by one of the following three routes using the indicated basic starting materials.

A. Acetylene/Formaldehyde (1) $HC{\equiv}CH + CH_2O \xrightarrow{Cat.} HOCH_2-C{\equiv}C-CH_2OH$ (2) $HOCH_2-C{\equiv}C-CH_2OH + H_2 \xrightarrow{Cat.} HOCH_2-CH_2-CH_2-CH_2OH$ (3) 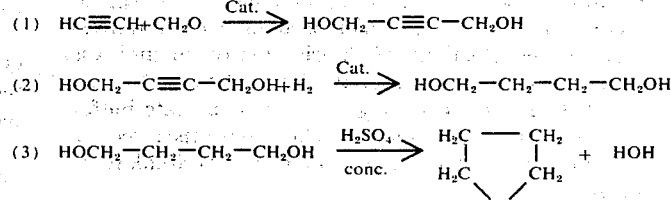

B. Furfural (1) 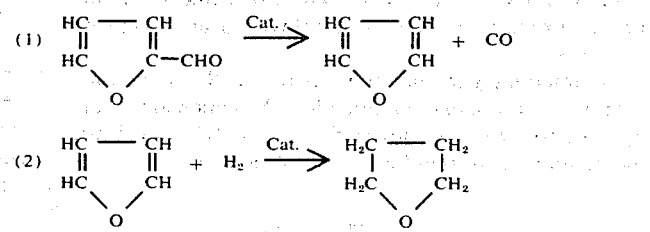

(2)

C. Butadiene/Chlorine (1) $H_2C{=}CH-CH{=}CH_2 + Cl_2 \xrightarrow{Cat.} ClCH_2CH{=}CH-CH_2Cl$ (2) $ClCH_2CH{=}CH-CH_2Cl + NaOH \rightarrow HOCH_2CH{=}CH-CH_2OH + 2NaCl$ (3) $HOCH_2CH{=}CH-CH_2OH + H_2 \xrightarrow{Cat.} HOCH_2-CH_2-CH_2-CH_2OH$ (4) 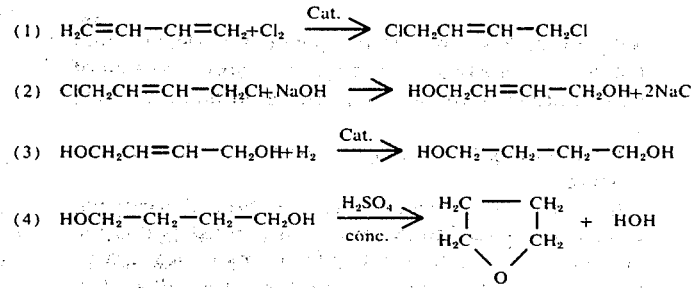

BACKGROUND OF THE INVENTION

1. Field of the Invention

The invention relates to the manufacture of tetrahydrofurans which are useful as solvents and polymer intermediates. In particular, the invention relates to the manufacture of tetrahydrofurans from corresponding gamma-chloroalkanols.

2. Prior Art

Tetrahydrofurans and particularly tetrahydrofuran (THF) itself are important products of commerce which find their principal utility as solvents and polymer intermediates. Of the many tetrahydrofurans, by far the most important commercially is THF which finds countless applications because of its excellent solvent properties. For example, THF is an excellent solvent for high molecular weight polyvinyl chloride resins and vinylidene chloride polymer used for top coating vinyl fabric and sheeting, coating cellophane, protective coatings, vinyl adhesives, printing inks and film coating. It is also used as solvent or reaction medium for synthetic polymers, natural resins, organometallic compounds, for Grignard reactions, hydride reductions, stereospecific polymerizations, condensations and esterifications. In addition, THF is useful as an intermediate for synthesis of pyrrolidine, tetrahydrothiophene and as a monomer or comonomer for certain polymerization reactions.

Though all three of the above-described processes are in commercial use, they nevertheless have certain disadvantages. For example, all three processes include an hydrogenation step which is quite high in its initial capital cost and, furthermore, requires extensive facilities for providing large amounts of hydrogen. In addition, processes based on acetylene are becoming more costly because of energy factors and the extraction of furfural from corn cobs or oat hulls is also quite expensive. Thus, there is clearly a need for alternative processes utilizing different starting materials to produce THF and other tetrahydorfurans in high yields and/or selectivity.

The cyclization of chlorobutanols to tetrahydrofuran is known in the prior art. The usual procedure is to treat the chlorobutanol with aqueous or alcoholic base (C. Walling and A. Padwa, J. Am. Chem. Soc., 83 2208 (1961); E. L. Jenner, J. Org. Chem., 27 1032 (1962); C. Walling and J. Bristol, J. Org. Chem., 37 3515 (1972). The thermal conversion of chlorobutanol does produce some tetrahydrofuran in addition to high boiling products. A partial conversion of tetramethylene chlorohydrin to THF in a system containing 1,4-dichlorobutane is reported in U.S. Pat. No. 2,950,232.

Until recently it was not considered synthetically possible to selectively chlorinate alkanols to chloroalkanols. Huyser (Methods in Free Radical Chemistry, Vol I, Marcel Kebber, N.Y. 1969) pointed out that photochlorination of alkanols was not a useful route to chloroalkanols because the reaction proceeds rapidly to oxidation with the formation of carbonyl compounds and chlorinated carbonyl compounds. However, Kollonitsch et al. (J. Chem. Soc. 1093 (1967)) showed that chlorination of butanol in liquid HF provided a mixture of 4-, 3- and 2-chlorobutanols with the 3-chloro-compound as the main product. Some improvement in the selectivity of chlorination of butanol was recently shown by Deno et al. (J. Org. Chem., Vol. 39 No. 4, P520 (1974)) using an aqueous acetate buffer system. However, no prior art is known for the selective chlorination of n-butanol to more than 50% 4-chloro-1-butanol.

BRIEF DESCRIPTION OF THE INVENTION

Applicant's invention is therefore directed to an improved process for making tetrahydrofurans comprising the steps a. contacting gamma-chloroalkanol with an aqueous protonic solution in the liquid phase by which alkanol is cyclized to form a tetrahydrofuran and HCl is evolved, the alkanol corresponding to the structure

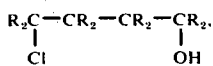

wherein the R groups are independently selected from the group consisting of hydrogen and alkyl, the sum of carbon atoms in the R groups being no more than 16; and b. separating the tetrahydrofuran from the reaction mixture.

In a preferred aspect of the invention, the gamma-chloroalkanol feed to the process is derived by dilution of a reaction mixture resulting from free radical chlorination of the corresponding unsubstituted alkanol in the presence of $H_2SO_4$.

In a second aspect of the invention, gamma-chloroalkanols suitable for cyclization to tetrahydrofuran are produced selectively by the liquid phase free radical chlorination of an alkanol corresponding to the structure

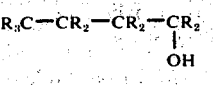

wherein the R groups are independently selected from the group consisting of hydrogen and alkyl, the sum of carbon atoms in the R groups being no more than 16. In particular, the reaction is carried out by contacting the alkanol with chlorine atoms in the presence of 50–96% wt. aqueous sulfuric acid.

As used herein, the term "gamma-chloroalkanol" refers to those alkanols in which the chlorine atom is attached to the third carbon atom removed from the carbon atom bearing the hydroxyl group, for example, 4-chloro-1-butanol.

DETAILED DESCRIPTION OF THE INVENTION

A. Cyclization

An essential aspect of the cyclization step is that the gamma-chloroalkanol must come in contact with both water and protons. Furthermore, since this reaction comes to an equilibrium and does not proceed to completion, it is necessary in order to obtain practical yields to remove the tetrahydrofuran from the system as it is formed. A particularly good way of doing this on either a batch or continuous basis is to use steam as both a source of water and as a source of energy to vaporize the tetrahydrofuran virtually as soon as it is formed.

The temperature of the cyclization is not particularly critical and can be carried out in the liquid phase at temperatures as low as room temperature. Likewise, the upper temperature limit of the reaction is not critical and is determined by the lower of either the decomposition temperature or the vaporization temperature of the gamma-chloroalkanol at whatever pressure is being used. However, to facilitate separation of the resultant tetrahydrofurans from the reaction mixture, it is preferred to use a temperature of 50°–200° C. It will be noted that steam distillation is a preferred method of removing tetrahydrofuran from the reaction system because it serves two functions; nevertheless, distillation under vacuum or at atmospheric or higher pressures may also be used as may be dictated by process economics.

The above-described process for making tetrahydrofurans by liquid phase cyclization of gamma-chloroalkanols is applicable to gamma-chloroalkanols corresponding to the structural formula

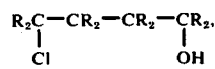

in which any of the R groups may be the same or different so long as the total number of carbon atoms in the R groups of the alkanol molecule do not exceed 16. Though $C_{20}$ chloroalkanols of this type are operable in the process, nevertheless it is preferred to use lower molecular weight materials the cyclization products of which are more easily vaporized and thus more easily separated. Thus $C_{4-10}$ chloroalkanols are preferred of which 4-chloro-1-butanol is of particular commercial value as a precursor to tetrahydrofuran.

A partial solution of a chloroalkanol in water alone is operably sufficient to constitute a protonic solution for the purpose of carrying out the cyclization reaction. However, it is preferred to employ aqueous solutions of protonic acids as the source of protons. By protonic acid is meant acid having a dissociation constant in water of at least about $1 \times 10^{-2}$. Quite dilute solutions of such acids, e.g. 0.1% by weight, are operable, concentrations of at least about 1% wt. being preferred. From the standpoint of its direct effect on the kinetics of the reaction, the upper limit of acid concentration is not critical. However, secondary considerations may make it preferable to limit acid concentrations. In this regard, when $H_2SO_4$ is employed as the protonic acid, it is desired to absorb the HCl evolved from the cyclization reaction into the acid and to retain it in the acid while the tetrahydrofuran is stripped out, by which contamination of the product with HCl can be avoided. However, the solubility of HCl in aqueous $H_2SO_4$ is insufficient at higher concentrations of $H_2SO_4$ to accomplish this. Therefore, $H_2SO_4$ concentrations of no more than about 40% wt. are preferred when $H_2SO_4$ is used as the source of protons.

B. Chlorination

The particular method for selective chlorination of 1-alkanol to the corresponding gamma-chloroalkanol is not critical in the sense of broad operability of the cyclization step as described hereinabove so long as there are no interfering reactive species present. However, the gamma chloroalkanol will ordinarily be made by free radical chlorination of the corresponding alkanol in the presence of aqueous 50–96% wt. sulfuric acid. This process can be carried out in several ways which differ mainly in the source of free radicals:

1. by addition to the reaction system of a free radical initiator such as an organic peroxide or azo compounds such as azobisisobutyronitrile;
2. photochemically by exposure of the reactants to ultraviolet light;
3. combinations of (1) and (2); and
4. by exposure of the reactants to high energy irradiation.

The source of the alkanol to be used in the process of the invention is not particularly critical technologically so long as any contaminants therein are not reactive or inhibitive. Thus, in the case of 1-butanol, it can be derived from any of the routes by which it is commonly prepared, e.g. by selective bacterial fermentation of carbohydrates, by the oxo-process or by the aldol process.

The chlorination is carried out in the liquid phase. Consequently, pressure of the process is not critical per se except as it relates to maintaining the liquid state of the normally liquid or solid components of the reaction system. It is not essential that the molecular chlorine be liquified; however, it is preferred in order to simplify the equipment demands of the process. The chlorination reaction is carried out at a temperature of from about −10° C to about 60° C. In order to obtain higher selectivity of the reaction for producing the gamma-chloroalkanol, it is preferred to carry out the chlorination reaction at 0°–30° C, a temperature of less than about 20° C being preferred.

The necessary residence time for the chlorination reaction is chiefly a function of the availability of chlorine in atomic form and ordinarily will be limited by the rate of removal of heat from the reaction, which is exothermic.

Like the cyclization stage, the chlorination step must also be conducted in protonated solution. However, in this case the protons are needed to avoid the reaction's proceeding to oxidation.

The chlorination reaction product contains, in addition to the gamma-chloroalkanol, lesser amounts of other chloroalkanols, unreacted 1-alkanol, HCl gas and, of course, $H_2SO_4$ and water. Thus, the reaction product must be fractionated to remove at least part of these materials. In all events, it is preferred to remove most of the HCl gas from the system since the presence of HCl will adversely affect the equilibrium of the subsequent cyclization reaction. This can be done most readily by steam distillation which results in both dilution of the chlorination reaction mixture with water and a raising of the solubility of HCl in the acid, which is advantageous when the chlorination reaction mixture is to be used as feed to the cyclization process stage. The chlorinated byproducts do not interfere with the cyclization of the gamma-chloroalkanol; therefore, it is not essential that they be removed prior to cyclization. However, provision must then be made for removing them subsequent to cyclization of the gamma-chloroalkanol.

The requirements for separation of by-products will vary widely depending upon both the method and composition of the 1-alkanol. In particular, the manufacture of higher tetrahydrofurans will entail more complex separation procedures than will the manufacture of lower molecular weight tetrahydrofurans such as THF. Nevertheless, the process of the invention is well exemplified by its use for the manufacture of THF.

A preferred embodiment of the invention is illustrated by FIG. 1 which is a simplified schematic representation of the process of the invention in which the cyclization and chlorination steps are integrated as a continuous process for the manufacture of THF.

Referring now to the Drawing, fresh 1-butanol is fed via line 1, admixed with recycled 1-butanol, which also contains small amounts of water, from line 3 and passed via line 5 to a mixing point where it is admixed with liquid chlorine from line 7 and 70% aqueous $H_2SO_4$ from line 9. The amount of butanol is in stoichiometric excess of that required to react in theory with the chlorine to obtain 4-chloro-1-butanol. The admixture of chlorine, 1-butanol and acid is then fed via line 11 to photochlorination reactor 100 wherein the mixture is exposed to ultraviolet light as a source of free radicals for initiation of the chlorination reaction. Premixing of the feed constitutents is, however, not critical and can be carried out inside the reactor itself if desired. The reaction product from the photochlorination reactor 100 is composed principally of 4-chloro-1-butanol, lesser amounts of 2- and 3-chloro-1-butanol byproducts, HCl gas, $H_2SO_4$, water and unreacted 1-butanol. Reaction product passes from the reactor 100 via line 13 to stripper 200 in which essentially all the HCl is removed overhead via line 15. The HCl-free bottoms from stripper 200 is removed via line 17 and passed to stripper 300 wherein it is stripped of THF by means of steam introduced to the column via line 21. To the extent that the steam admitted to column 300 is insufficient to dilute the acid in the feed thereto to below about 40% weight $H_2SO_4$, the feed is diluted with water from line 19 prior to being fed to column 300. The THF stripped from the reaction mixture is removed overhead via line 23 while the stripper bottoms is passed via line 25 to distillation column 400. Essentially all the HCl produced in the cyclization reaction is absorbed into the relatively dilute $H_2SO_4$.

Column 400 is also a fractionation or splitting column in which the organic components of the reaction and some water are separated from the $H_2SO_4$ by vaporization and removed via line 27, condensed and then passed to decanter 500 in which the overhead condensate separates into an upper water-insoluble layer containing 2- and 3-chloro-1-butanol and unreacted 1-butanol and a lower water-soluble layer containing some 1-butanol dissolved in water. The upper water-insoluble layer is passed via line 29 to stripper 600 in which 1-butanol is stripped out, condensed and returned to the process via line 3. Bottoms from stripper 600 are removed from the process via line 31. The lower water-soluble layer from decanter 500 is removed via line 33. This layer, which is comprised mainly of water containing unreacted 1-butanol dissolved in water, is then fed to stripper 700 in which the azeotrope of 1-butanol with water is vaporized overhead along with a small amount of water and passed from the stripper through line 35 to butanol recycle line 3. The bottoms fraction is almost entirely water and is removed via line 37 to plant water treatment facilities before being reused or returned to its source.

The bottoms from column 400 is mainly dilute aqueous $H_2SO_4$ in which HCl gas is absorbed. This bottoms fraction is, of course, too dilute for direct recycle to the chlorination step. Thus, it must be reconcentrated to a concentration of at least 50% weight $H_2SO_4$. As is shown here, a preferred method of reconcentrating the acid is to purge a portion of the acid from the process via line 41 to concentrate the remaining dilute acid by adding concentrated $H_2SO_4$ via line 43 and then to pass the more concentrated acid via line 39 to HCl stripper 800, in which the HCl and water are removed overhead through line 45. By reconcentrating the acid before the HCl stripper, the solubility of the HCl in the $H_2SO_4$ is substantially decreased and much less energy is therefore needed to strip out the HCl. The bottoms from HCl stripper 800 is essentially HCl-free $H_2SO_4$ which is fed to the chlorination reactor via lines 9 and 11.

The invention can also be observed by reference to the following examples:

EXAMPLE I

In this example, 4-chloro-1-butanol was produced by photochlorination of 1-butanol in 70% aqueous $H_2SO_4$ and cyclized to form THF. 200 Ml of 70% $H_2SO_4$ were charged to a glass reactor fitted with magnetic stirrer, thermometer, inlet fritted-glass diffusion disc, and a port for metered injection of butanol below the surface of the aqueous sulfuric acid. The reactor system was purged with a slow stream of nitrogen. Using a 275 watt sun lamp for ultraviolet irradiation, both butanol and chlorine were added slowly to the reactor while maintaining the temperature in the range of $-10°$ C. to $+10°$ C. At the end of the reaction, the reactor contents were poured over ice and diluted to 1 liter. Distillation through a small distillation column provided an organic product containing tetrahydrofuran, unreacted 1-butanol, 2-chloro-1-butanol, and 3-chloro-1-butanol. The weight of this mixture was 40.8 g based upon 28.3 g of n-butanol and 12 g of chlorine. The ratio of THF to combined 2- and 3-chlorobutanols was 66/34 (1.9).

EXAMPLE II

The process of Example I was repeated using instead 60% aqueous $H_2SO_4$ at 3°–15° C. The reactor product was quenched on ice and diluted with water. Distillation through a small Vigreux still produced a two-layer system. From a run using 29.6g of n-butanol and 25 g of chlorine an organic product weighing 26.8 g was recovered. The ratio of THF to 2-chloro- and 3-chloro-1-butanol products was 50/50 (1.0). Thus, the selectivity of the process for making THF was somewhat less using 60% acid than when 70% acid was used.

EXAMPLE III

When the procedure of Example I was repeated using 96% sulfuric acid, chlorination proceeded rapidly at a temperature range of 10°–18° C and the weight ratio of THF to 2-chloro- and 3-chloro-1-butanol in the cyclized product was 39 to 61 (0.6). A small amount of other byproducts was also detected.

EXAMPLE IV

Using 200 ml of 70% $H_2SO_4$ and sun lamp irradiation in the manner of Example I, n-butanol and chlorine were injected slowly over a 60 minute period while maintaining the temperature at 38°–46° C. Using 38.2 g of n-butanol and 12 g of $Cl_2$, upon dilution and distillation, a cyclized product was obtained weighing 33.1 g in which the ratio of tetrahydrofuran to combined 2-chloro- and 3-chloro-1-butanol was 60/40 (1.5).

EXAMPLE V

When the procedure of the previous examples was used with 80% $H_2SO_4$ at 10°–22° C, the weight ratio of THF to 2-chloro- and 3-chloro-1-butanol was 52 to 48 (1.1). Again, a small amount of other byproducts was obtained.

EXAMPLE VI

The facile conversion of 4-chloro-1-butanol to THF is illustrated by this example in which 5 g of 4-chloro-1-butanol were mixed with 20% sulfuric acid and the mixture was distilled at 107°–112° C. The first 2.6 grams overhead were essentially pure THF.

EXAMPLE VII

In this example, instead of using aqueous sulfuric acid as the protonating agent for the cyclization reaction, aqueous 4-chloro-1-butanol was used as a proton source. Five grams of freshly distilled 4-chloro-1-butanol and 50 ml distilled water were mixed and distilled at 95°–101° C into four fractions which were collected at the refluxing still head at 66°–100° C. The first fraction which boiled at 66°–70° C contained 1.3 grams of essentially pure THF. The second fraction contained 1.6 grams of THF with a small amount of water. The last two fractions contained decreasing amounts of THF and increasing amounts of water. The water content of all fractions was strongly acidic primarily as a result of the HCl dissolved therein.

EXAMPLE VIII

When the procedure of Example I was repeated at 0°–10° C using aqueous 36% HCl, the reaction was quite unselective. The ratio of THF to combined 2- and 3-chloro-alkanol was only 31/79 (0.4).

EXAMPLE IX

When the procedure of Example I was repeated at 10°–25° C using aqueous trifluoroacetic acid, the reaction once more was quite unselective, the ratio of THF to 2- and 3-chlorobutanols being only 38/62 (0.6).

EXAMPLE X

When bromine was substituted for chlorine in the procedure of Example I, it was necessary to heat the reactants to over 50° C to obtain substantial reaction. Furthermore, the reaction resulted in a considerable degree of oxidation. Clearly chlorine is preferred to bromine in the practice of this invention.

I claim:

1. A process for making a tetrahydrofuran comprising:

a. contacting gamma-chloroalkanol with a dilute aqueous protonic solution in the liquid phase at a temperature of 50°–200° C by which the alkanol is cyclized to form a tetrahydrofuran and HCl is evolved and absorbed into the protonic solution, the alkanol corresponding to the structure

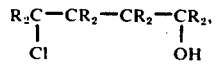

wherein the R groups are independently selected from the group consisting of hydrogen and alkyl, the sum of carbon atoms in the R groups being no more than 16; and b. separating the tetrahydrofuran from the reaction mixture.

2. The process of claim 1 in which the tetrahydrofuran is removed from the reaction mixture by distillation.

3. The process of claim 1 in which the water for contacting the liquid gamma-chloroalkanol is provided in the form of steam in sufficient quantity to effect separation of the tetrahydrofuran by steam distillation.

4. The process of claim 2 in which the tetrahydrofuran is separated from the reaction mixture by vacuum distillation.

5. The process of claim 1 in which the gamma-chloroalkanol is 4-chloro-1-butanol.

6. The process of claim 1 in which the gamma-chloro-alkanol is derived from the aqueous free radical chlorination of a corresponding nonchlorinated alkanol in the presence of aqueous $H_2SO_4$ having a concentration of 50–96% weight $H_2SO_4$, basis total weight of $H_2SO_4$ and water dissolved therein.

7. The process of claim 6 in which the gamma-chloroalkanol and solution of $H_2SO_4$ are derived by removal of HCl from and by dilution with water of the reaction mixture from the liquid phase photochlorination of a corresponding non-chlorinated alkanol in the presence of aqueous $H_2SO_4$ having a concentration of 50–96% weight $H_2SO_4$, basis total weight of $H_2SO_4$ and water dissolved therein.

8. The process of claim 7 in which
 a. the reaction mixture from which tetrahydrofuran has been removed is fractionated into (1) an overhead fraction containing vaporizable organics and water and (2) a bottoms fraction consisting essentially of aqueous $H_2SO_4$ and absorbed HCl,
 b. the acid bottoms fraction is concentrated to at least 50% weight $H_2SO_4$,
 c. the concentrated acid is stripped of HCl and
 d. the stripped acid is recycled to the photochlorination step.

9. A process for the liquid phase free radical chlorination of 1-butanol comprising contacting the 1-butanol with chlorine atoms in the presence of 50–96% wt. aqueous sulfuric acid at a temperature of from about −10° C to about 60° C.

* * * * *